(12) United States Patent
Sugita et al.

(10) Patent No.: US 6,692,953 B1
(45) Date of Patent: Feb. 17, 2004

(54) PORTABLE AIR-BORNE BACTERIA SAMPLER

(75) Inventors: Naoki Sugita, Tokyo (JP); Yutaka Hatta, Tokyo (JP); Takeshi Yamada, Tokyo (JP); Yukihiro Nakata, Tokyo (JP)

(73) Assignee: Midori Anzen Co., Ltd., Tokyo (JP)

( * ) Notice: Subject to any disclaimer, the term of this patent is extended or adjusted under 35 U.S.C. 154(b) by 0 days.

(21) Appl. No.: 10/130,120

(22) PCT Filed: Nov. 17, 2000

(86) PCT No.: PCT/JP00/08130

§ 371 (c)(1),
(2), (4) Date: Aug. 6, 2002

(87) PCT Pub. No.: WO01/38483

PCT Pub. Date: May 31, 2001

(30) Foreign Application Priority Data

Nov. 25, 1999 (JP) .......................................... 11-334201

(51) Int. Cl.$^7$ ................................................ C12M 1/26
(52) U.S. Cl. .................................................. 435/309.1
(58) Field of Search .................... 435/309.1; 73/863.21, 73/863.41, 863.53, 864.71

(56) References Cited

U.S. PATENT DOCUMENTS

| | | | | | |
|---|---|---|---|---|---|
| 3,968,012 | A | * | 7/1976 | Jones | 435/309.1 |
| 5,421,214 | A | * | 6/1995 | Burgdorfer | 73/863.22 |
| 6,040,153 | A | * | 3/2000 | Lemonnier | 435/30 |
| 6,133,020 | A | * | 10/2000 | Pitzurra | 435/287.1 |
| 6,294,375 | B1 | * | 9/2001 | Chevalier | 435/287.1 |

FOREIGN PATENT DOCUMENTS

| | | |
|---|---|---|
| EP | 0964240 | 12/1999 |
| JP | 568300 | 9/1993 |
| JP | 11225743 | 8/1999 |
| WO | WO0024865 | 5/2000 |

* cited by examiner

*Primary Examiner*—David A. Redding
(74) *Attorney, Agent, or Firm*—Varndell & Varndell, PLLC

(57) ABSTRACT

Nozzle openings 15a each including a straight duct portion 15s and a tapered portion 15t are situated at an upstream position of an air flow with respect to the straight duct portion. The nozzle openings are formed in a nozzle plate 15 such that the nozzle openings 15a are arranged in grid, and airborne microorganisms passing through the nozzle plate 15 can be effectively collected to form colonies. A degree of cleanness is measured by counting the colonies visually.

8 Claims, 8 Drawing Sheets

PORTABLE AIR-BORNE BACTERIA SAMPLER

TECHNICAL FIELD

The present invention relates to a portable type airborne microorganism sampler for collecting airborne microorganisms in a room for monitoring and managing a pollution due to microorganisms.

TECHNICAL FIELD

There have been proposed a stationary type airborne microorganism sampler and a portable type airborne microorganism sampler for monitoring a condition of microorganism pollution by collecting airborne microorganisms such as bacteria and fungi in pharmaceutical factories and food factories and public spaces such hospitals. Particularly, portable type airborne microorganism samplers have been used for managing and checking a pollution within a space where a high degree of cleanness is required such as biological clean room and manufacturing lines in the pharmaceutical factories as well as in a space where care and management for microorganism pollution are required such as hospitals.

Figure 12:
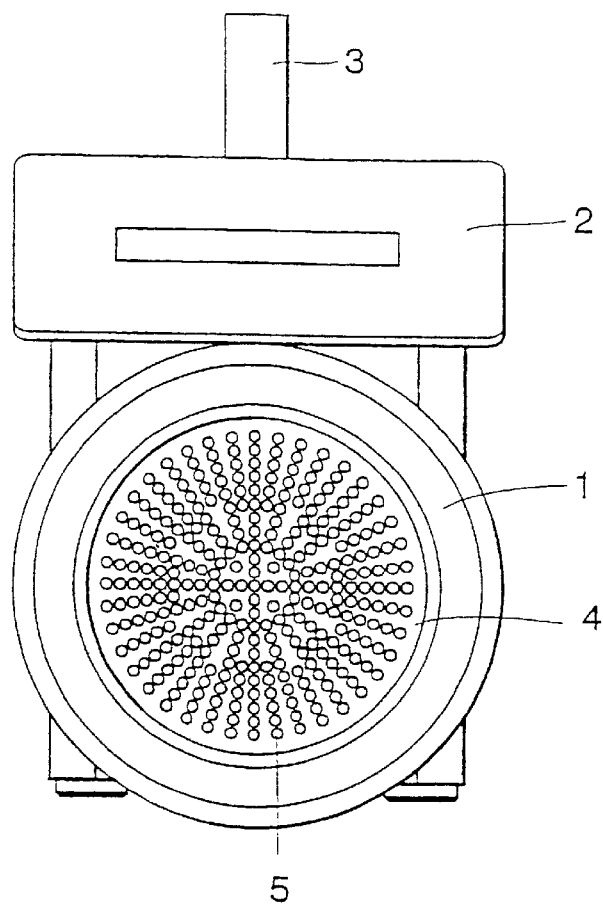
FIG. 12 is a plan view illustrating a known sampler.

FIG. 12 is a plan view showing a known portable type sampler, which is mainly consisting of a collecting section 1 and an operating section 2. The operating section 2 has a handle 3 by means of which a user can carry the sampler. At a front end of the collecting section 1, there is clamped a nozzle portion 4 through which an air is introduced for collecting airborne microorganisms. The nozzle portion 4 has a number of openings 5 arranged radially.

Figure 13:
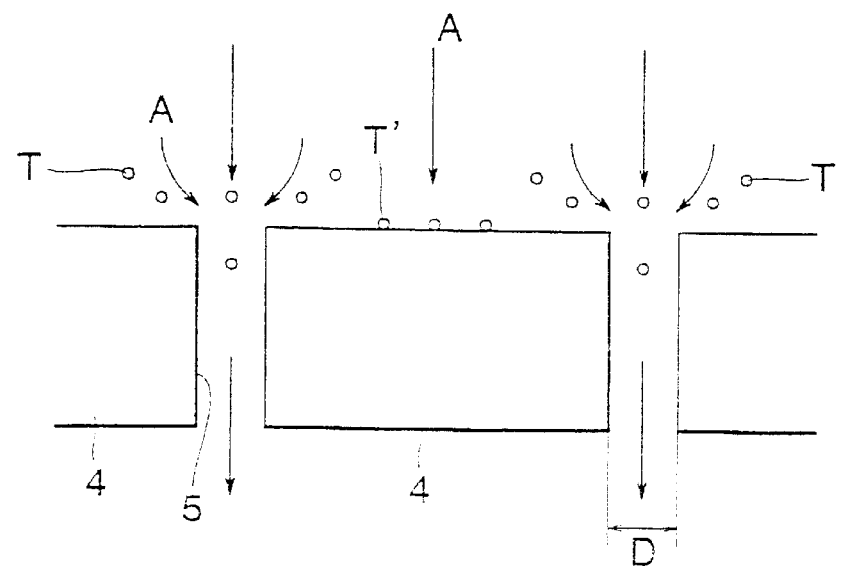
FIG. 13 is an explanatory view showing a condition of adhesion of bacteria on to a flat portion between nozzles.

In the sampler constructed in the manner explained above, when a power switch is made on to rotate a fan, as illustrated in FIG. 13, an air flow A containing particles T to be tested such as bacteria and fungi floating near the sampler is sucked into the sampler through nozzle openings 5. The thus sucked air flow A passes through the nozzle openings 5 and impinges against a culture medium K and particles T are collected by the culture medium K.

(1) However, in the known portable type sampler mentioned above, the nozzle openings 5 are arranged radially, and therefore the number of nozzle openings 5 per a unit area varies over a surface of the nozzle plate 4. This results in that an amount of air flow passing through a unit area of the nozzle plate varies, and in a area of a larger amount of air, the culture medium is liable to be dried and a collection efficiency for microorganisms in the particles T might be decreased and even after microorganisms are arrested, colonies of microorganisms are not easily formed. Moreover, in an area in which distances between adjacent nozzle openings 5 are too short, collected microorganisms come close to each other and colonies of microorganisms come also close to each other. Then, the number of colonies could not be detected accurately. Furthermore, since colonies of microorganisms are arranged irregularly in a radial manner, the number of colonies could not be counted precisely by miscounting unless special counting methods or separate colony counters are applied.

(2) The air flow A including particles T to be detected does not flow smoothly at flat surface portions between adjacent nozzle openings 5 and particles T' which is a part of particles T are liable to be adhered onto these flat portions. In practice, it has been experimentally confirmed by a microscope that a large number of particles T' in the air flow A are adhered onto the flat portions. Moreover, in an area in which adjacent nozzle openings 5 come extremely close to each other, the air flow A is temporally stagnant and particles T' are accumulated extraordinarily.

When a sampler is used in a clean environment such as a clean room in which a highly clean space is realized, microorganisms adhered onto an upper surface of the nozzle plate 4 without passing through the nozzle openings 5 are destroyed not being arrested by the culture medium. In the clean environment, since the number of bacteria passing through the nozzle openings 5 and collected by the culture medium K is inherently small, the number of microorganisms actually impinged upon the culture medium K and collected thereby becomes very small. Therefore, it is very difficult to judge whether a degree of cleanness is actually high or the measurement could not be conducted precisely.

The present invention has for its object to provide a portable type airborne microorganism sampler, in which the above mentioned problem (1) can be solved, an amount of air flow passing through a unit area of the nozzle can be uniform, and the number and positions of colonies formed in the culture medium by collected airborne microorganism can be confirmed precisely and easily.

It is another object of the invention to provide a portable type airborne microorganism sampler, in which the above mentioned problem (2) can be solved, airborne microorganisms can be collected effectively even under a clean environment having a small number of microorganisms, stagnant of the air flow can be suppressed, and a degree of cleanness can be estimated with a high precision.

DISCLOSURE OF THE INVENTION

According to the invention, a portable type airborne microorganism sampler comprising a nozzle plate having a plurality of openings formed therein, a nozzle holder supporting said nozzle plate, a chalet holder supporting a chalet containing a culture medium and arranged at a downstream position of an air flow, and a fan generating the air flow, characterized in that each of said nozzle openings includes a straight duct portion and a tapered conical portion which is widened toward an upstream of the air flow, and the nozzle openings are at cross points between orthogonal lateral and longitudinal lines, said lateral lines extending parallelly and equidistantly and said longitudinal lines extending parallelly and equidistantly.

According to further aspect of the invention, a portable type airborne microorganism sampler comprising a nozzle plate having a plurality of openings formed therein, a nozzle holder supporting said nozzle plate, a chalet holder supporting a chalet containing a culture medium and arranged at a downstream position of an air flow, and a fan generating the air flow, characterized in that each of said nozzle openings includes a straight duct portion and a tapered conical portion widened toward an upstream of the air flow, and the nozzle openings are arranged at cross points between a plurality of lateral reference lines extending parallelly and equidistantly and a plurality of parallel lines which extend equidistantly and are inclined with respect to the lateral reference lines by 60 degrees and 120 degrees.

BEST MODE OF THE INVENTION

Now the invention will be explained with reference to embodiments shown in FIGS. 1 to 11.

Figure 1:
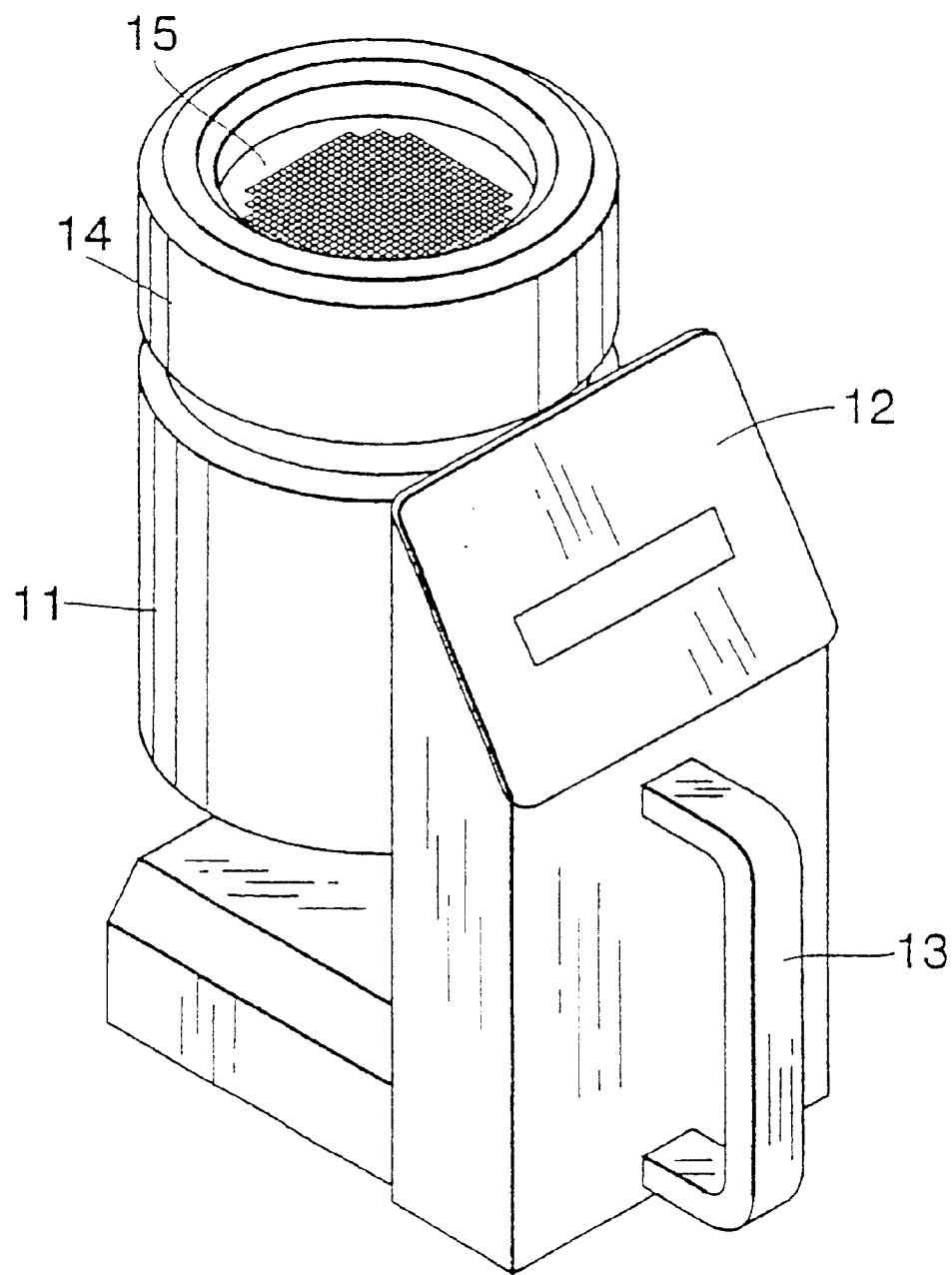
FIG. 1 is a perspective of an embodiment of the sampler according to the invention.
Figure 2:
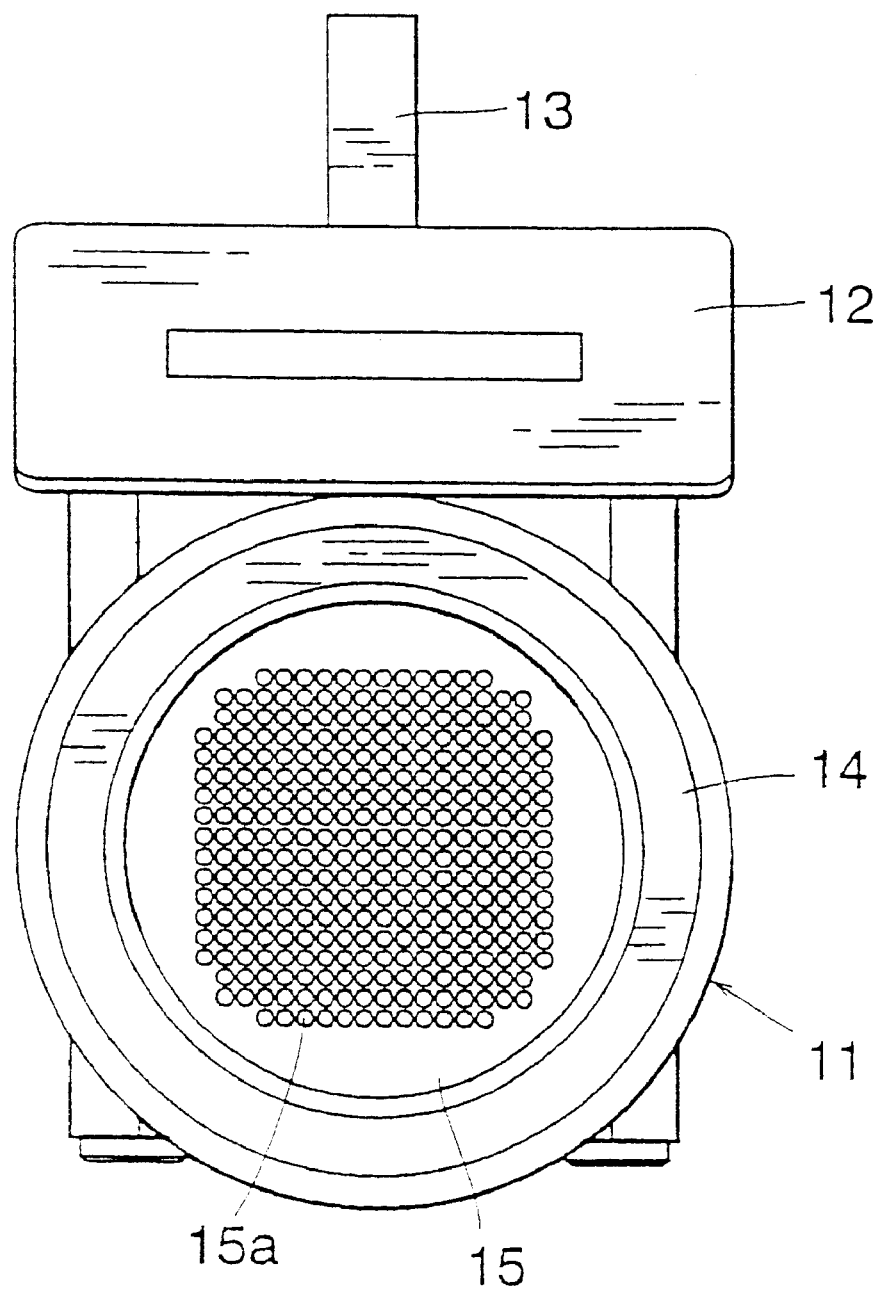
FIG. 2 is a plan view thereof.
Figure 3:
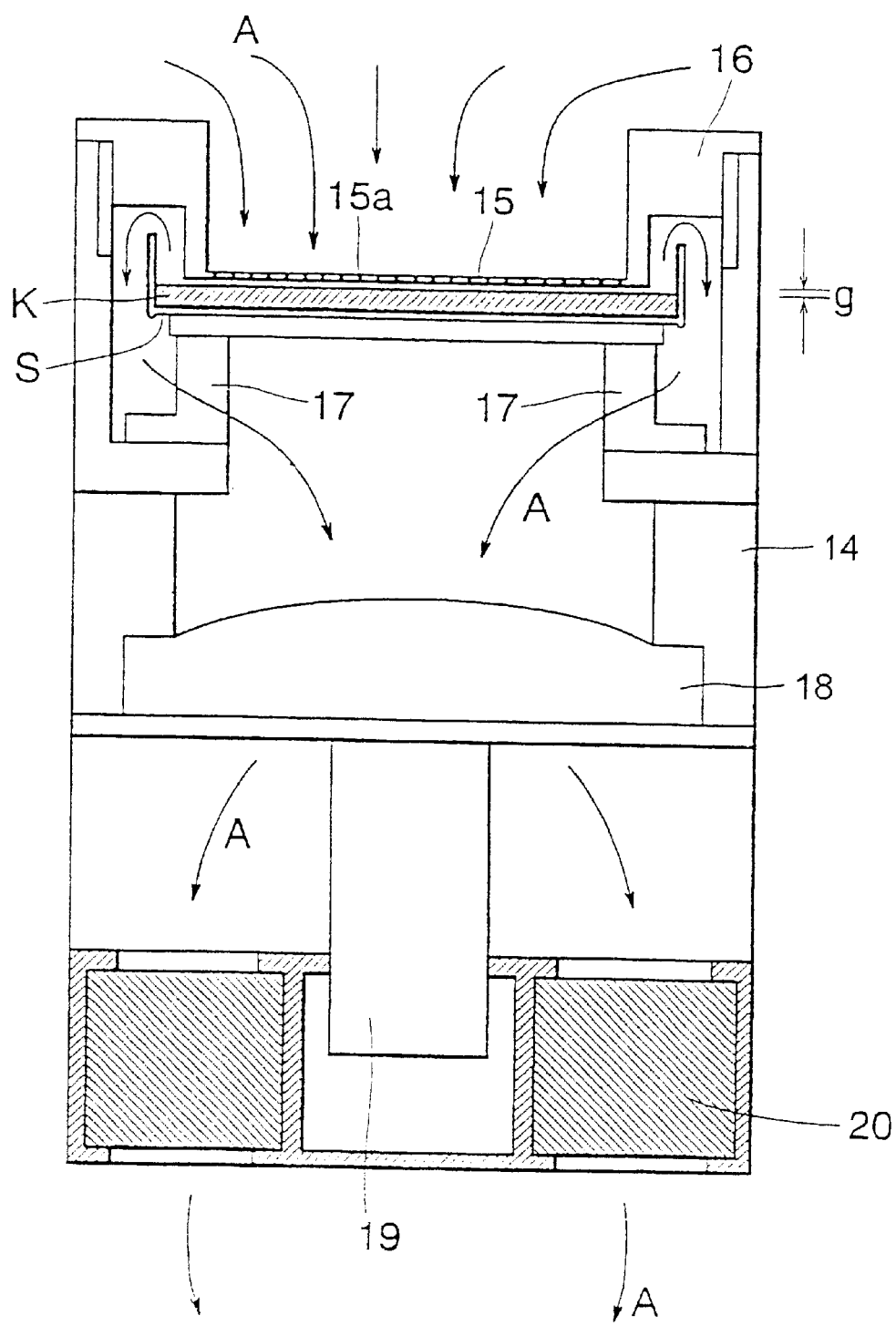
FIG. 3 is a cross sectional view of a collecting portion.
Figure 4:
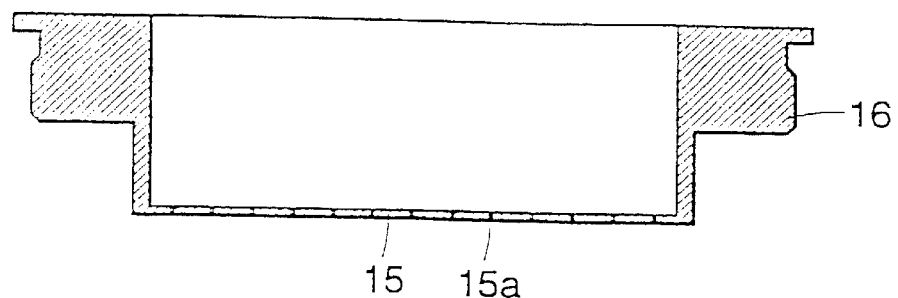
FIG. 4 is a cross sectional view of a nozzle.

FIG. 1 is a perspective view showing the portable type airborne microorganism sampler according to the invention, FIG. 2 is a plan view thereof, and FIG. 3 is a cross sectional view thereof. The portable type sampler is mainly composed of a collecting section 11 for collecting airborne microorganisms and an operating section 12. The operating section 12 includes a grip 13 for carrying the sampler. The collecting section 11 comprises a cylindrical housing 14 and a nozzle plate 15 having a number of fine nozzle openings 15a formed therein in matrix, said nozzle being supported by a nozzle support 16 at a top of the housing 14 as illustrated in FIG. 4. In order to avoid a leakage of air, the nozzle support 16 is screwed to the housing 14.

Immediately below the nozzle plate 15 is arranged a chalet S containing a culture medium K such as Japan agar, said chalet being supported by a chalet holder 17. A distance g between the nozzle plate 15 and an upper surface of the culture medium K is set to 0.5–1.5 mm. Within a space formed underneath the chalet holder 17, there are arranged a high static pressure fan 18 such as turbofan and vortex blower, a motor 19 for driving the high static pressure fan 18 and a control circuit. In order to attain a high collection efficiency, a wind speed of the air flow passing through the nozzle plate 15 is set to be not lower than 20 m/sec. An exhaust filter 20 is arranged at a lowermost position of the housing 14.

Upon operation, the chalet S having the culture medium K contained therein with a given thickness is supported by the chalet holder 17 within the housing 14, and then the nozzle holder 16 is clamped at the top of the housing 14. When the motor 19 is driven to rotate the high static pressure fan 18, an air is introduced through the nozzle openings 15a and flows though a space between the nozzle 15 and the culture medium K. When the wind speed of the air flow A through the nozzle plate 15 is set to be not lower than 20 m/sec, the culture medium K serves as a collection plate, and airborne microorganisms such as bacteria and fungi are impacted against a surface of the culture medium K by inertia force and are collected thereby. After that, the air flow A is sucked by the high static pressure fan 18 through a space formed in a circumferential portion and is exhausted through the exhaust filter 20 as shown by arrows in FIG. 3.

In case of measuring airborne microorganisms within a clean room having a certain degree of cleanness, an amount of window processed by the sampler within ten minutes is set to 100+L/min which is determined in accordance with ISO standards. In this case, the nozzle plate 15 is formed by an aluminum plate having a thickness t of 2.3 mm in order that the nozzle plate is not deformed by a cutting process.

In the airborne microorganism sampler, it is important that airborne microorganisms can be collected by the culture medium K with a high collection efficiency and that airborne microorganisms are not arrested by portions other than the culture medium. To this end, a direction and an intensity of the air flow A are changed abruptly at the surface of the culture medium K to attain a high collection efficiency, and at the same time a direction and an intensity of the air flow A are not changed abruptly at portions except for the culture medium such that airborne microorganisms are not arrested by these portions. Portion at which the air flow A is changed most abruptly except for the culture medium K are upper edge portions of the nozzle plate 15. Therefore, in order not to make the air flow A free from the abrupt change, the nozzle opening is formed to have a straight duct portion 15s and a tapered portion 15t which is opened widely toward the upstream of the air flow A.

Figure 5:
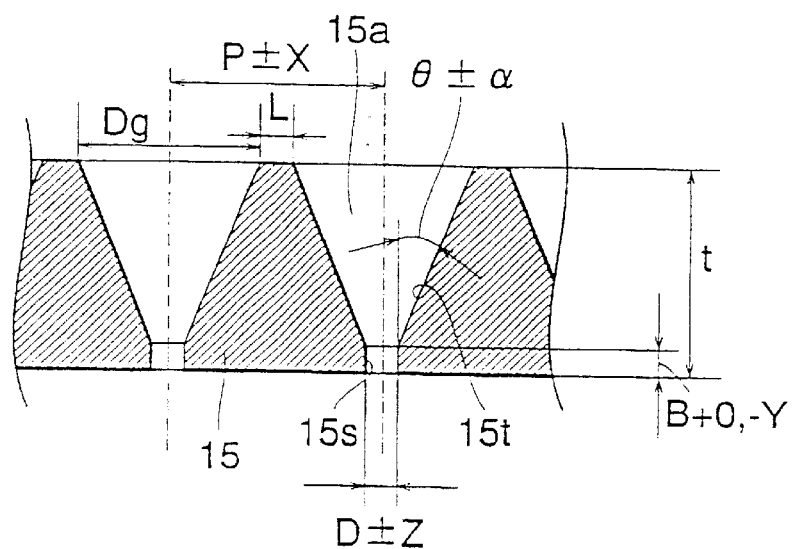
FIG. 5 is a cross sectional view of an opening of the nozzle.

When the nozzle opening 15a is formed by the straight duct portion 15s and the tapered portion 15t widened upwardly as illustrated in FIG. 5, in order to suppress a pressure loss, it is preferable to make a length of the straight duct portion 15s as small as possible. By considering a possible error upon manufacturing, a length of the straight duct portion 15s is set to 0.3[+0, −0.1] mm=B[+0, −Y]. The collection efficiency on the culture medium K is improved by increasing a wind speed of the air flow through the straight duct portion 15s, and this wind speed is inversely proportional to an inner diameter of the straight duct portion 15s. It has been experimentally confirmed that an inner diameter of the straight duct portion 15s is preferably set to 0.36±0.01 mm=D±Z(0, 1017 mm$^2$) while taking into mind of the collection efficiency and working precision.

If the nozzle opening 15a is formed only by the straight duct portion 15s, a pressure loss upon sucking is increased. Therefore, according to the invention, the tapered portion 15t is provided above the straight duct portion 15s. When a taper angle of the tapered portion 15t is too large, the number of the nozzle openings 15a formed in the nozzle plate 15 is limited. Therefore, in the present embodiment, the tapered portion 15t is formed such that a taper angle is set to 45±2 degrees, that is to say a half taper angle of the tapered portion 15t is set to 22.5±1 degrees=θ+α. A depth of the tapered portion 15t is equal to a difference between the thickness of the nozzle plate 15 and a length of the straight duct portion 15 of 0.3 mm, i.e. 2.0 mm. Then, a widest diameter Dg of the uppermost portion of the tapered portion 15t is 2.02 mm.

A diameter of the nozzle plate 15 is determined by an inner diameter of 85 mm φ of the chalet S and is set to 73 mm. Then, a surface area of the nozzle plate is 4185 mm$^2$. The nozzle openings 15a are arranged in a grid-like manner at cross points between mutually orthogonal plural lateral and longitudinal lines extending parallelly and equidistantly such that the number of colonies formed by microorganisms arrested and cultured by the culture medium K can be easily measured with naked eyes. In this manner, the nozzle openings 15a are arranged such that centers of these openings situate at cross points between a plurality of lateral straight lines extending parallelly with a pitch P=2.4 mm and a plurality of longitudinal straight lines extending parallelly with the same pitch over a whole surface of the nozzle plate 15. Moreover, some nozzle openings are formed in a peripheral portion of the nozzle plate 15 such that parts of these openings are lacked. Then, the total number of the nozzle openings 15a becomes about 710. In the present embodiment, there are formed 713 nozzle openings 15a are formed. A distance L between an edge of a widest diameter portion of a tapered portion 15t and an opposing edge of a widest diameter portion of an adjacent tapered portion 15t has to be set a suitable value with taking into consideration of a working error. In the present embodiment, the distance L is set to 0.38 mm while the pitch P of nozzle opening is set to 2.4±0.1 mm=P±X.

If the nozzle openings 15a apart too far from each other, the number of the nozzle openings formed in the nozzle plate 15 is decreased and a collection efficiency becomes lower. Moreover, a distance L becomes too large, and a flat surface area on the nozzle plate 15 and a larger number of airborne microorganisms might be adhered onto the flat portion. Furthermore, the air flow might be stagnated temporarily. Therefore, in order to suppress undesired adhesion of microorganisms onto the flat surface of the nozzle plate 15 at an upstream of the air flow, it is necessary to make the distance L smaller.

On the other hand if the nozzle openings 15a are closer to each other to decrease the distance L too much, although the flat portion 15f of the nozzle plate 15 can be reduced, at an area between adjacent tapered portions 15t, the air flow A is liable to stagnate temporarily and a large number of particulate substances are adhered onto the nozzle plate. If the nozzle openings 15a are further closer to each other such that the widest diameter portions of adjacent nozzle openings are overlapped, there are formed sharp edges between adjacent nozzle openings. Then, upon cleaning the nozzle plate 15, a cleaning cloth might be cut by the sharp edges and debris thereof might be adhered to the nozzle plate. The collection of particulate substances might be affected by debris. Moreover, the sharp edge might injure fingers of users.

Figure 6:
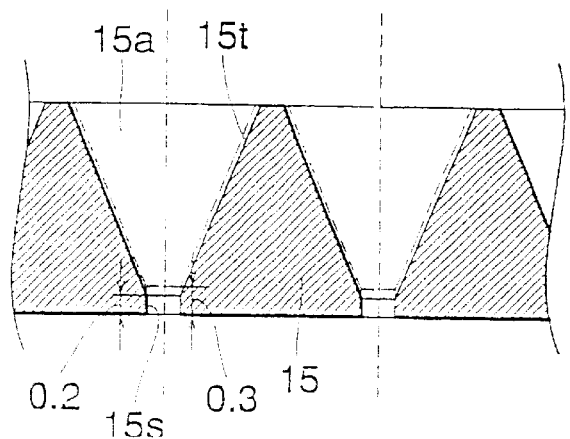
FIG. 6 is a cross sectional view of a nozzle opening when a straight duct portion is shortened.

In the present embodiment, a length of the straight duct portion 15s is set to 0.3 mm. A tolerance of working for making the nozzle openings is about [+0, −0.1]. Now it is assumed that a length of the straight duct portion 15s is reduced to 0.2 mm as shown in FIG. 6, the widest diameter of the tapered portion 15t is increased by 0.0414×2 mm and amounts to 2.02+0.083=2.103 mm.

Figure 7:
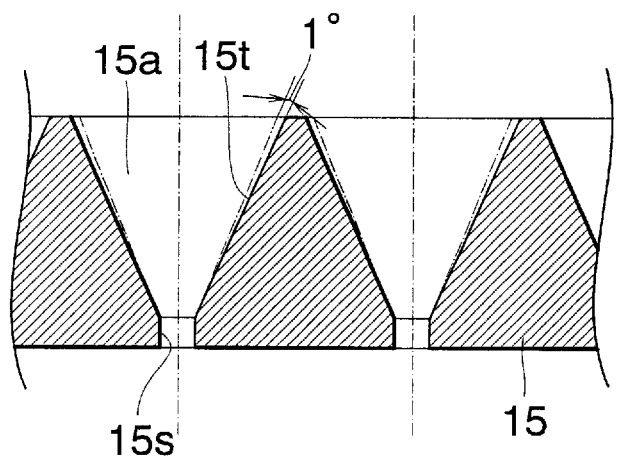
FIG. 7 is a cross sectional view showing a nozzle opening when an angle of a tapered portion is increased.

Furthermore, as illustrated in FIG. 7, a taper angle of the tapered portion 15t might be increased by two degrees due to a tolerance in working precision. Then, the widest diameter of the tapered portion 15t is increased by 0.0413×2 mm and amounts to 2.02+0.083=2.103 mm.

Therefore, if the above increments in the length of the straight duct portion 15s and the taper angle of the tapered portion 15t occur at the same time, the widest diameter of the tapered portion 15t is increased by 0.16 mm and amounts to 2.186 mm. Furthermore, if these increments occur at adjacent nozzle openings 15a at the same time, the distance L between widest diameter portions of adjacent tapered portions 15t is decreased by 0.166 mm.

Upon forming the nozzle openings, positions of adjacent spindles of the machine tool might be shifted by 0.1 mm. Then, the distance L might be further reduced by 0.2 mm. Therefore, the pitch P of the nozzle openings is preferably determined such that the above mentioned errors can be absorbed. That is to say, if the pitch P is set to 2.3 mm, adjacent tapered portions 15t might be overlapped. In the present embodiment, the pitch P is set to 2.4 mm.

The length L of the widest diameter portions of adjacent tapered portions 15t is given by the following equation:

$$L=(P\pm X)-(D\pm Z)-2[\{t-(B+0,-Y)\}\tan(\theta\pm\alpha)]$$

A maximum deviation δmax=Lmax−Lmin is determined in the following manner:

$$\text{Lmax}=(P+X)-(D-Z)-2[\{t-(B+0)\}\tan(\theta-\alpha)]$$

$$\text{Lmin}=(P-X)-(D+Z)-2[\{t-(B-Y)\}\tan(\theta+\alpha)]$$

Now the above mentioned tolerances in working are expressed as follows:
X=0.1 mm, Y=0.1 mm, Z=0.01 mm, θ=22.5 degrees, α=1 degree, t=2.3 mm and B=0.3 mm.

Then, the maximum deviation may be denoted by the following equation:

$$\begin{aligned}
\delta\max &= 2X + 2Z + 2[(t-B)\{\tan(\theta+\alpha) - \tan(\theta-\alpha)\} + Y\tan(\theta+\alpha)] \\
&= 0.2 + 0.02 + 2 \times [2 \times (0.435 - 0.394) + 0.1 \times 0.435] \\
&= 0.2 + 0.02 + 2 \times (0.082 + 0.0435) \\
&= 0.2 + 0.02 + 0.251 \\
&= 0.47057 \cdots \approx 0.47
\end{aligned}$$

In this manner, the length L between the widest diameter portions of adjacent nozzle openings is preferable set to $0 \leq L \leq 0.47$.

Figure 8:
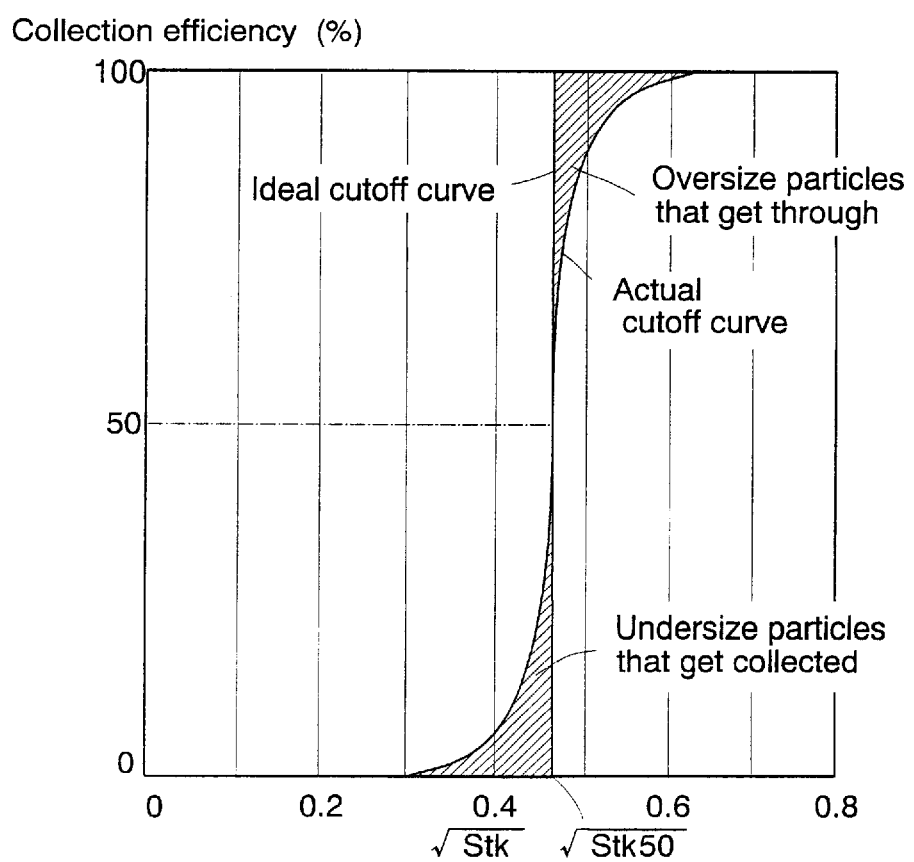
FIG. 8 is a graph depicting a relationship between a limit particle size and a collection efficiency.
Figure 9:
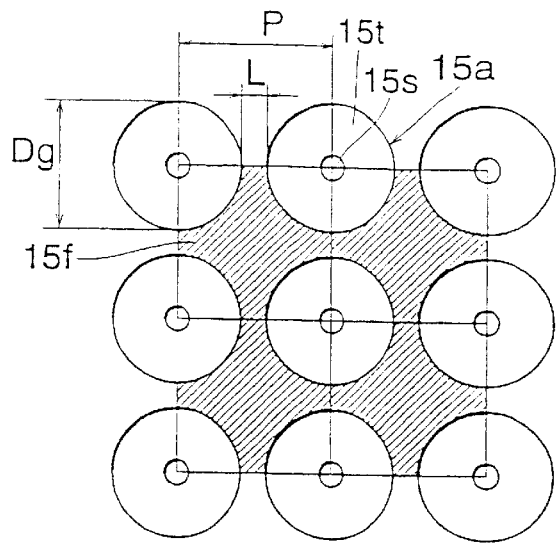
FIG. 9 is a plan view of nozzle openings when nozzles are arranged at corners of a square.

According to an ideal graph representing a relationship between a limit particle size and a collection efficiency shown in FIG. 8 (Aerosol Technology, page 114, FIG. 5.8, "Ideal and Practice of Limit Particle Size of Impact", published on Apr. 10, 1985 from INOUE SHOIN Co. Ltd. Japan), when it is desired to attain a collection efficiency not lower than 50%, a Stokes number $S_{tk}$ is preferably set to be not lower than 0.22 ($S_{tk}^{1/2}$ not lower than 0.47), when it is desired to realize a collection efficiency not lower than 95%, a Stokes number Stk is preferably set to be not lower than 0.3 $S_{tk}^{1/2}$ not lower than 0.55). It should be noted that the Stokes number $S_{tk}$ may be defined by the following equation, wherein a particle density is ρ, a particle size is d, a wind speed U, Cunningham constant C, an air viscosity η, and a nozzle opening inner diameter D.

$$S_{tk}=\rho d^2UC/9\eta D \qquad (1)$$

In the present embodiment, 713 nozzle openings 15*a* are formed in the nozzle plate 15 having a diameter of 73 mm. Now following values are applied in the equation (1): a density of particulate substance $\rho=1\times10^{-3}$ kg/cm³, a diameter of particulate substance d=0.7 μm which is substantially equal to hay bacillus, a viscosity of air $\eta=1.847\times10^{-6}$ kgf·s/m²×9.8⁻ m/sec², an inner diameter of nozzle D=0.36+0.01=0.37 mm, which is required to confirm the effectiveness even through a nozzle diameter is increased by 0.01 mm due to a tolerance in manufacturing, and a wind speed U=21.78 m/s, which is obtained by dividing 100 L/min by a total area of the nozzle openings. Then, a stokes number $S_{tk}$ becomes smaller than 0.22.

Therefore, the number of the nozzle openings 15*a* is reduced such that a Stokes number $S_{tk}$ becomes larger than 0.22. To this end, eight nozzle openings 15*a* are removed from each of quadrants divided by horizontal and vertical lines are removed in a symmetrical manner with respect to the four quadrants. Therefore, 32 nozzle openings are removed and the total number of nozzle openings becomes 681, while a pitch P of the nozzle openings is not changed. Then, a wind speed becomes 24.04 m/s which is higher than 20 m/s.

As illustrated in FIG. 9, when the nozzle openings 15*a* having the widest diameter Dg=2.02 mm are arranged with a pitch P=2.4 mm, a surface area of the flat portion 15*f* denoted by hatching except for the straight duct portion 15*s* and tapered portion 15*t* of the nozzle openings 15*a* within an imaginary square obtained by connecting centers of four adjacent nozzles amounts to 44.4% of the imaginary square.

Figure 10A:
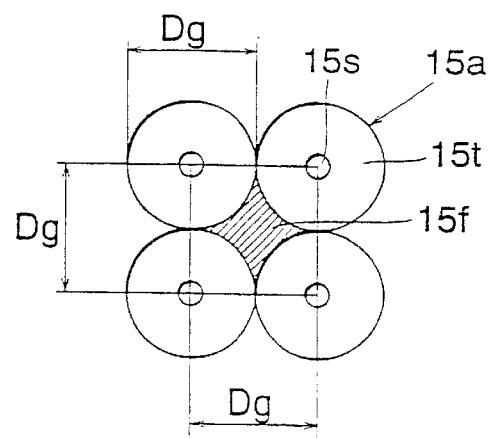
FIGS. 10(a) and 10(b) are a plan view of nozzle openings when nozzles are arranged corners of square.
Figure 10B:
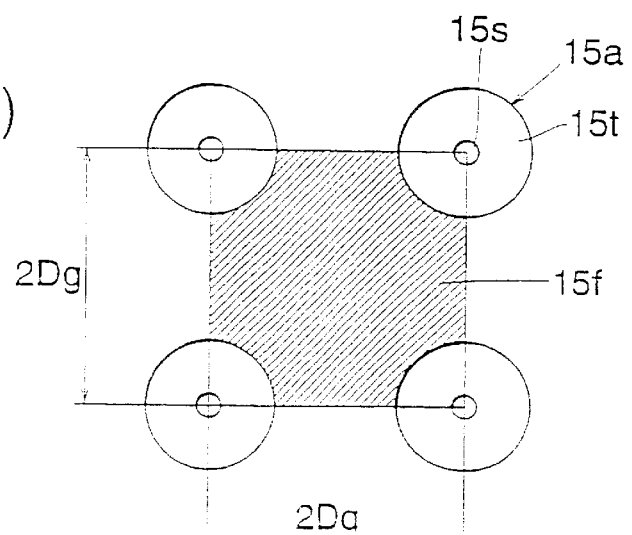

FIG. 10(*a*) shows a case, in which the nozzle openings 15*a* arranged such that the widest diameter portions of tapered portions 15*t* of adjacent nozzle openings are brought into contact with each other. Then, a ratio of a surface area of the flat portion 15*f* to a surface area of the imaginary square becomes 21.5%. If the distance L between the widest diameter portions of adjacent nozzle openings 15*a* is set to a half of the widest diameter of the nozzle opening L=Dg/2, a ratio of a surface area of the flat portion 15*f* to a surface area of the imaginary square amounts to 65.1%. Furthermore, if the distance L between the widest diameter portions of adjacent nozzle openings 15*a* is set to the widest diameter of the nozzle opening L=Dg as depicted in FIG. 10(*b*), a ratio of a surface area of the flat portion 15*f* to a surface area of the imaginary square becomes 80.3%.

As explained above, in order to obtain a wind speed higher than a give value, the number of the nozzle openings 15*a* has to be not less than 681. Then, the pitch P should be not larger than 2.48 mm, and therefore the length L has to be not larger than 0.46 mm. In this case, a ratio of a surface area of the flat portion 15*f* to a surface area of the imaginary square amounts to 44.4%. Therefore, it is preferable to arrange the nozzle openings 15*a* such that a ratio of a surface area of the flat portion 15*f* to a surface area of the imaginary square amounts to 21.5–44.4%.

Figure 11A:
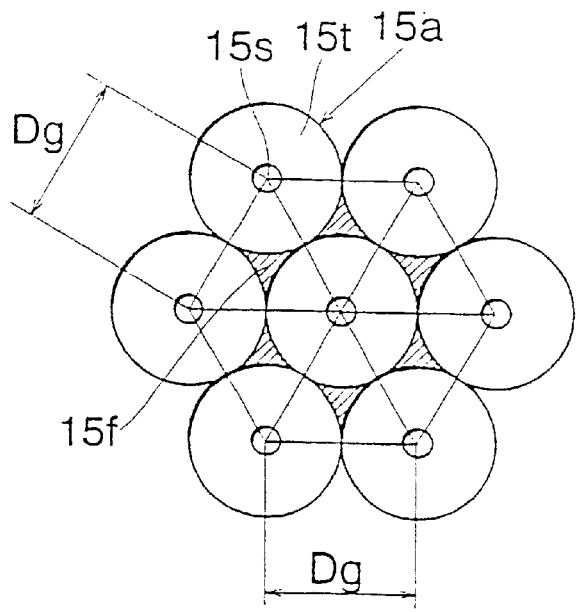
FIGS. 11(a) and 11(b) are a plan view of nozzle openings when nozzles are arranged at corners of a triangle.
Figure 11B:
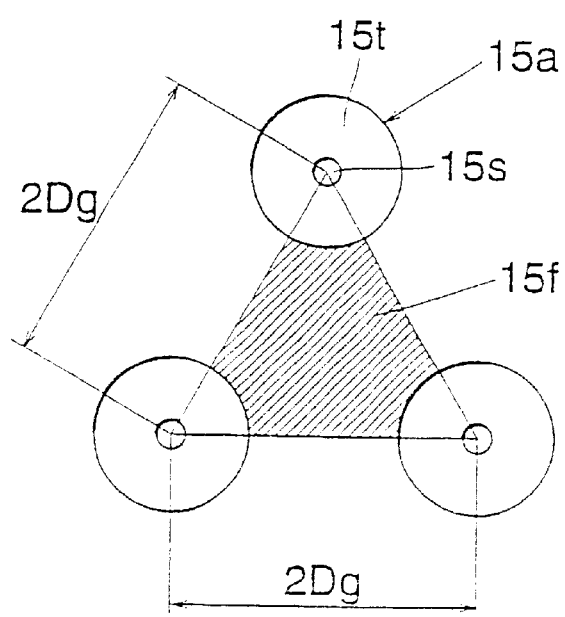

According to the invention, it is not always necessary to arrange the nozzle openings in grid, but they may be arranged as depicted in FIG. 11(*a*), in which centers of nozzle openings 15*a* situate at apexes of equilateral triangles connected continuously in all directions. That is to say, the nozzle openings may be arranged at cross points between a plurality of equidistant lateral reference lines extending in parallel and a plurality of equidistant oblique lines extending in parallel and being inclined with respect to the reference lines by 60 degrees and 120 degrees. In this manner, minimum distances between adjacent nozzle openings 15*a* can be obtained in all directions.

In this case, operation of counting colonies becomes somewhat cumbersome, but a surface area of the flat portion 15*f* can be minimized. When the widest diameter portions of adjacent tapered portions 15*t* are brought into contact with each other as illustrated in FIG. 11(*a*), a ratio of a surface area of the flat portion 15*f* to a surface area of an imaginary triangle amounts to 9.3%. When a side of the imaginary triangles is set to twice the widest diameter of tapered portion 15*t* as shown in FIG. 11(*b*), a ratio of a surface area of the flat portion 15*f* to a surface area of the imaginary triangle amounts to 77.3%.

In this manner, a surface area of the flat portion 15*f* of the nozzle plate 15 can be minimized, the number of bacteria which are adhered to the flat portion and are destroyed thereon can be reduced, and particulate substances passing through the nozzle openings 15*a* and adhered onto the culture medium K can be effectively sampled. Therefore, due to the same reason as that explained with reference to the imaginary square arrangement, it is preferable to arrange the nozzle openings 15*a* such that a ratio of a surface area of the flat portion to a surface area of the imaginary triangle amounts to 9.3–73.9%.

APPLICABILITY IN THE INDUSTRIAL FIELD

As explained above, in the portable type airborne microorganism collecting sampler according to the invention, a nozzle opening is formed by the straight duct portion and the conical tapered portion situating at an upstream with respect to the straight duct portion, and a plurality of nozzle openings are arranged in equidistant grids or at apexes of equilateral triangles continuously connected in all directions. A high speed wind can be attained with a small loss, airborne microorganisms can be collected effectively even in a clean environment having a smaller number of airborne microorganisms, and a degree of cleanness can be measured with a high precision.

What is claimed is:

1. A portable airborne microorganism sampler comprising a nozzle plate having a plurality of openings formed therein, a nozzle holder supporting said nozzle plate, a chalet holder supporting a chalet containing a culture medium and arranged at a downstream position of an air flow, and a fan generating the air flow, characterized in that each of said nozzle openings includes a straight duct portion and a tapered conical portion which is widened toward an upstream of the air flow, and the nozzle openings are at cross points between orthogonal lateral and longitudinal lines, said lateral lines extending parallel and equidistantly and said longitudinal lines extending parallel and equidistantly.

2. The portable airborne microorganism sampler according to claim 1, wherein said nozzle openings are arranged such that widest diameter portions of the tapered portions of adjacent nozzle openings are not overlapped with each other.

3. The portable airborne microorganism sampler according to claim 2, wherein said nozzle openings are arranged such that centers of adjacent nozzle openings are separated by a distance which is substantially equal to a widest diameter of the widest diameter portions.

4. The portable airborne microorganism sampler according to claim 1, wherein said nozzle openings are arranged such that a distance L between widest diameter portions of adjacent nozzle openings is set to $0 \leq L \leq 4.7$ mm.

5. The portable airborne microorganism sampler according to claim 1, wherein said nozzle openings are arranged such that a ratio of a surface of a flat portion except for said tapered portion with respect to a surface area of a square defined by centers of four adjacent nozzle openings amounts to 21.5–80.3%.

6. A portable airborne microorganism sampler comprising a nozzle plate having a plurality of openings formed therein, a nozzle holder supporting said nozzle plate, a chalet holder supporting a chalet containing a culture medium and arranged at a downstream position of an air flow, and a fan generating the air flow, characterized in that each of said nozzle openings includes a straight duct portion and a tapered conical portion widened toward an upstream of the air flow, and the nozzle openings are arranged at cross points between a plurality of lateral reference lines extending parallel and equidistantly and a plurality of parallel lines which extend equidistantly and are inclined with respect to the lateral reference lines by 60 degrees and 120 degrees.

7. The portable airborne microorganism sampler according to claim 2, wherein said nozzle openings are arranged such that widest diameter portions of the tapered portions of adjacent nozzle openings are not overlapped with each other.

8. The portable airborne microorganism sampler according to claim 6, wherein said nozzle openings are arranged such that a ratio of a surface of a flat portion except for said tapered portion with respect to a surface area of a equilateral triangle defined by centers of three adjacent nozzle openings amounts to 9.3–77.3%.

* * * * *

UNITED STATES PATENT AND TRADEMARK OFFICE
CERTIFICATE OF CORRECTION

PATENT NO. : 6,692,953 B1
DATED : February 17, 2004
INVENTOR(S) : Naoki Sugita et al.

It is certified that error appears in the above-identified patent and that said Letters Patent is hereby corrected as shown below:

Column 8,
Line 36, change "$0 \leqq L \leqq 4.7$ mm" to -- $0 \leqq L \leqq 0.47$ mm --.

Signed and Sealed this

Thirty-first Day of August, 2004

JON W. DUDAS
*Director of the United States Patent and Trademark Office*